United States Patent
Sano et al.

(10) Patent No.: US 10,598,611 B2
(45) Date of Patent: Mar. 24, 2020

(54) X-RAY PHASE IMAGING APPARATUS AND METHOD OF DETECTING DEFECT OF MATERIAL CONTAINING FIBERS

(71) Applicant: Shimadzu Corporation, Kyoto (JP)

(72) Inventors: Satoshi Sano, Kyoto (JP); Taro Shirai, Kyoto (JP); Takahiro Doki, Kyoto (JP); Akira Horiba, Kyoto (JP); Naoki Morimoto, Kyoto (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 21 days.

(21) Appl. No.: 16/033,739

(22) Filed: Jul. 12, 2018

(65) Prior Publication Data
US 2019/0025232 A1 Jan. 24, 2019

(30) Foreign Application Priority Data
Jul. 20, 2017 (JP) .................................. 2017-140647

(51) Int. Cl.
*G01N 23/041* (2018.01)
*A61B 6/00* (2006.01)

(52) U.S. Cl.
CPC .......... *G01N 23/041* (2018.02); *A61B 6/4035* (2013.01); *A61B 6/4291* (2013.01); *A61B 6/484* (2013.01); *G01N 2223/615* (2013.01); *G01N 2223/646* (2013.01); *G21K 2207/005* (2013.01)

(58) Field of Classification Search
CPC ....... G01N 2223/646; G01N 23/20075; G01N 2223/615; G01N 23/041; A61B 6/4035; A61B 6/4291; A61B 6/484
See application file for complete search history.

(56) References Cited

U.S. PATENT DOCUMENTS

2014/0270060 A1* 9/2014 Date ................ G01N 23/20075
378/36
2015/0031986 A1* 1/2015 Bernhardt ................ A61B 6/12
600/424

FOREIGN PATENT DOCUMENTS

JP 2014-211344 A 11/2014
JP 2017-072399 A 4/2017

OTHER PUBLICATIONS

Shimadzu Corporation, inspeXio SMX-225CT FPD HR (webpage), available from <https://www.an.shimadzu.co.jp/ndi/products/x_ryct/smx_225ct_f pd_hr08.htm > (Apr. 5, 2016) [English version of webpage also provided].
Shimadzu Corporation, inspeXio SMX-225CT FPD HR, (webpage that is English version of <https://www.an.shimadzu.co.jp/ndi/products/x_ryct/smx_225ct_f pd_hr08.htm>), available from <https://www.shimadzu.com/an/ndi/ct/smx-225ct_fpd_hr08.html > (Apr. 5, 2016).
Extended European Search Report dated Oct. 23, 2018 in the corresponding European patent application No. 18181911.1.

(Continued)

*Primary Examiner* — Chih-Cheng Kao
(74) *Attorney, Agent, or Firm* — Muir Patent Law, PLLC

(57) ABSTRACT

This X-ray phase imaging apparatus is provided with a control unit that acquires information on a defect of a material based on a dark field image of the material.

16 Claims, 8 Drawing Sheets

First and Second Embodiments

(56) References Cited

OTHER PUBLICATIONS

Pfeiffer et al: "Hard-X-ray dark-field imaging using a grating interferometer," Nature Materials, vol. 7, pp. 134-137, Jan. 13, 2008.

Mayo et al: "In-Line Phase-Contrast X-ray Imaging and Tomography for Materials Science," Materials, ISSN, 1996-1944, pp. 1-28, Dec. 2012.

* cited by examiner

First and Second Embodiments

First and Second Embodiments

Self-image  Absorption grating

First and Second Embodiments

Self-image  Absorption grating

First and Second Embodiments

Self-image  Absorption grating

First and Second Embodiments

First and Second Embodiments

First Embodiment
Dark field image
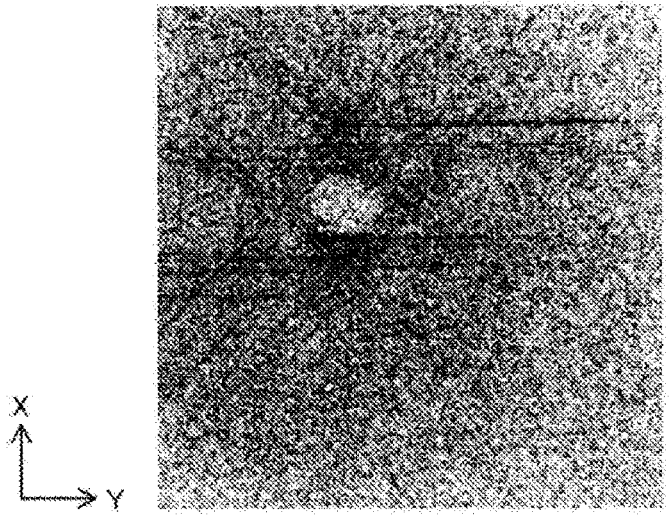
FIG. 5
First Embodiment
Dark field image
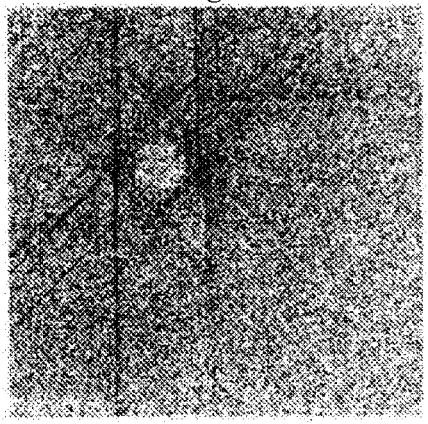
First Embodiment
Synthesized dark field image
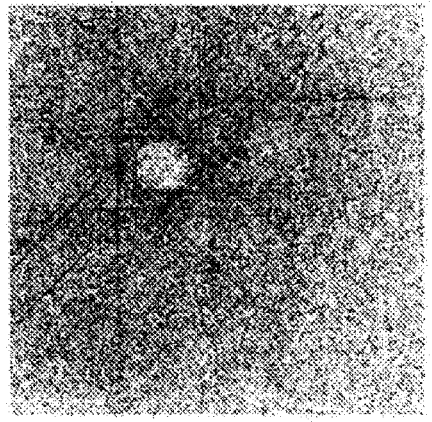
FIG. 6A
FIG. 6B

Second Embodiment

Dark field image

Luminance value plot

Second Embodiment

Modification of first embodiment

All shown in red lines

Modification of first embodiment

All shown in green lines

Modification of first embodiment

Modification of First Embodiment

X-RAY PHASE IMAGING APPARATUS AND METHOD OF DETECTING DEFECT OF MATERIAL CONTAINING FIBERS

CROSS-REFERENCE TO RELATED APPLICATIONS

The priority application number JP2017-140647, entitled "X-ray phase imaging apparatus and method of detecting defect of material containing fibers", filed on Jul. 20, 2017, invented by Satoshi Sano, Taro Shirai, Takahiro Doki, Akira Horiba, and Naoki Morimoto, upon which this patent application is based is hereby incorporated by reference.

BACKGROUND OF THE INVENTION

Field of the Invention

The present invention relates to an X-ray phase imaging apparatus and a method of detecting a defect of a material containing fibers.

Description of Background Art

Conventionally, a method of observing a material containing fibers using X-ray CT is known. Such an X-ray phase imaging apparatus and a method of detecting a defect of a material containing fibers are disclosed in, for example, Japanese Unexamined Patent Application Publication No. 2014-211344.

In Japanese Unexamined Patent Application Publication No. 2014-211344, a method is described in which dispersibility and orientation of carbon fibers in a carbon fiber reinforced plastic are imaged by X-ray CT. Specifically, X-rays are irradiated onto a carbon fiber reinforced plastic as a subject from an X-ray source equipped in an X-ray CT apparatus, and based on the detection result by a detector (a result based on the absorption of the X-rays by the carbon fiber reinforced plastic) of the X-ray CT apparatus, the inside of the carbon fiber reinforced plastic is imaged.

In the carbon fiber reinforced plastic, in addition to carbon fibers, metal coated carbon fibers may be dispersed therein. Since the X-ray absorption coefficient of the metal coating the carbon fibers is smaller than the absorption coefficient of carbon fibers or plastics, contrast in the X-ray CT can be obtained, which enables an image of the metal coated carbon fibers to be acquired. The non-metal coated carbon fibers and metal coated carbon fibers in such reinforced plastics may utilize the same carbon inside, and therefore the orientation and the dispersibility are similar. In other words, by grasping the dispersibility and the orientation of non-metal coated carbon fibers, it is possible to grasp the dispersibility and the orientation of non-metal coated carbon fibers. Even in cases where a defect exists in a carbon fiber reinforced plastic, it is possible to acquire information of the defect by imaging the defect portion by X-ray CT.

In general, in an X-ray CT apparatus, in order to resolve minute defects in a carbon fiber reinforced plastic, it is necessary to image a subject (defects in a carbon fiber reinforced plastic) in an enlarged manner to such a degree that the resolution by a pixel can be performed. For this reason, when imaging defects in a carbon fiber reinforced plastic in X-ray CT, there is a problem that the observable field of view at a particular time is restricted.

SUMMARY OF THE INVENTION

In order to attain the aforementioned object, an X-ray phase imaging apparatus according to a first aspect of the present invention includes: an X-ray source configured to irradiate X-rays to material containing fibers as a subject; an image signal detector configured to detect an image signal based on the X-rays irradiated from the X-ray source; a plurality of gratings arranged between the X-ray source and the image signal detector, the plurality of gratings including a first grating to which the X-rays from the X-ray source are irradiated and a second grating to which the X-rays which have passed through the first grating are irradiated; an image acquisition unit configured to acquire a dark field image representing an attenuation rate of X-ray interference intensity in a case in which the material is present and in a case in which the material is not present based on the image signal detected by the image signal detector; and a control unit configured to acquire information on a defect of the material based on the dark field image of the material acquired by the image acquisition unit.

Here, in an X-ray phase imaging apparatus in which X-rays are irradiated to a material via a plurality of gratings, in cases where X-rays are irradiated to a material in which minute defects exist, X-rays are refracted due to the difference between the refractive index in the defect and the refractive index around the defect. Furthermore, in cases where the boundary between the defect and the peripheral portion thereof has a complicated shape, X-rays will be multiply refracted to be diffused depending on the shape. In this case, the self-image (interference fringe formed when X-rays have passed through the first grating) formed in the vicinity of the position where the second grating is arranged is partially weakened in the interference intensity by the diffusion of the X-rays. As a result, in the self-image (interference fringe), the difference between the interference intensity of the portion corresponding to the defect and the interference intensity of the other portion becomes relatively large.

The dark field image is obtained from a step curve (the curve representing the change in luminance value when the second grating is moved relative to the interference fringe) obtained based on interference intensity. Therefore, by acquiring information on the defect of the material based on the dark field image acquired based on the interference intensity, even in cases where the size of the defect is smaller than the pixel size of the image signal detector and therefore the defect cannot be detected by the absorption image, in the self-image (interference fringe), the difference between the interference intensity of the portion corresponding to the defect and the interference intensity of the other portion becomes relatively large. Therefore, the defect can be detected by the dark field image. Therefore, by configuring such that the control unit acquires the information on the material defect based on the dark field image of the material acquired by the image acquisition unit, it becomes possible to acquire the information on the defect of the material based on the dark field image without enlarging the image. That is, it is possible to acquire the information on the defect of the material while suppressing restriction of the observable field of view at one time. As a result, it is possible to easily observe the entire length of a relatively long defect, and it is possible to easily detect the defect ratio (damage degree) in the entire material.

Generally, in an X-ray CT apparatus or the like, in the case of observing a light element like a carbon fiber reinforced plastic, in many cases, X-rays of an energy region of soft X-rays are used. In such a case, when a subject is thick, the energy of X-rays that pass through the object becomes high, so that it is difficult to give contrast. On the other hand, in an X-ray phase imaging apparatus in which X-rays are irradiated to a material via a plurality of gratings, in general, X-rays with slightly higher energy than the region of energy of soft X-rays often arrive at the detector. Nevertheless, the refraction and the diffusion of X-rays due to the defect in the subject can be captured. Thus, in the X-ray phase imaging apparatus according to the present invention, even for a relatively thick material or a material covered with some material, it is possible to easily observe the material with X-rays.

In the X-ray phase imaging apparatus according to the aforementioned first aspect of the present invention, preferably, the control unit is configured to acquire information on at least one of a length and a quantity of one or more cracks which is the defect of the material based on the dark field image of the material acquired by the image acquisition unit. With this configuration, it is possible to easily detect the ratio of the defect (damage state) in the material based on at least one of the length and the quantity of the one or more cracks.

In this case, preferably, the control unit acquires a total value of luminance values of a pixel line composed of a plurality of pixels along a predetermined direction in the dark field image of the material acquired by the image acquisition unit, acquire data of a change in the total value along a direction orthogonal to the predetermined direction, and acquire information on a depth in addition to the length of the crack which is the defect of the material based on the acquired data. With this configuration, by acquiring the information on the depth of the crack in addition to the length of the crack based on the total value of the luminance value of each pixel line, the total value of the luminance values reflects both the length and the depth of the crack. Therefore, it is possible to easily detect the region (pixel line) where the ratio of the defect is large (the damage is large) in the dark field image.

In the X-ray phase imaging apparatus according to the aforementioned first aspect of the present invention, preferably, the control unit is configured to display a region surrounded by a crack which is the defect of the material and acquire an area of the region in the dark field image of the material acquired by the image acquisition unit. With this configuration, by displaying the region and acquiring the area of the region, it is possible to more clearly grasp the damage degree of the material.

In the X-ray phase imaging apparatus according to the aforementioned first aspect of the present invention, preferably, the material includes a resin in addition to the fibers, and the control unit is configured to acquire information on at least one of a length of and a quantity of one or more impregnation defective parts of the resin which is the defect of the material based on the dark field image of the material acquired by the image acquisition unit. With this configuration, in addition to the defect of fibers, based on at least one of the length and the quantity of the one or more impregnation defective parts of the resin, it is possible to easily detect the ratio of the defect in the material (damage state).

In the X-ray phase imaging apparatus according to the aforementioned first aspect of the present invention, preferably, the control unit is configured to acquire information on the defect of the material based on the dark field image acquired by the image acquisition unit by moving either one of the first grating and the second grating in a direction orthogonal to an optical axis direction of the X-rays. In general, in a method (so-called fringe scanning method) of acquiring a dark field image by moving either one of the first grating and the second grating in a direction orthogonal to the optical axis direction of X-rays, as compared with a method of acquiring a dark field image by rotating either one of the first grating and the second grating in a plane orthogonal to the optical axis direction of X-rays (so-called moire single imaging method), it is possible to obtain a clear image. That is, the fringe scanning method is particularly effective for detecting minute defects in a material.

In the X-ray phase imaging apparatus according to the aforementioned first aspect of the present invention, preferably, the control unit is configured to perform fringe scanning by relatively changing an extending direction of each of a grating component of the first grating and a grating component of the second grating in a grating plane with respect to the material and acquire information on the defect of the material based on a dark field image obtained by synthesizing a plurality of the dark field images acquired by the image acquisition unit. Here, the defect formed in the direction in which each of the grating component of the first grating and the grating component of the second grating extends is mainly acquired in the dark field image. Therefore, by acquiring a synthesized dark field image by relatively changing the extending direction of each of the grating component of the first grating and the grating component of the second grating, as compared with the case where information on defects is acquired from only a single dark field image, it is possible to acquire information on more defects.

Further, by acquiring the information on the defect based on the synthesized dark field image, as compared with a case in which the information on the defect is individually acquired plural times in each of a plurality of dark field images in case of acquiring the information on the defects once in the synthesized dark field image, the required time can be shortened.

In the X-ray phase imaging apparatus according to the aforementioned first aspect of the present invention, preferably, the plurality of gratings is disposed between the X-ray source and the first grating and includes a third grating for enhancing coherence of the X-rays irradiated from the X-ray source. Here, in an X-ray phase imaging apparatus, in some cases, the focal spot size of the X-ray source is reduced in order to enhance the coherence of X-rays. In this case, since the dose from the X-ray source is reduced, the time required for the measurement may sometimes become longer. Therefore, by providing the third grating for enhancing the coherence of the X-rays irradiated from the X-ray source, it is possible to enhance the coherence of the X-rays without reducing the focal spot size of the X-ray source. With this, as compared with the case of reducing the focal spot size of the X-ray source, it becomes possible to shorten the time required to acquire the defect information of the material.

A method of defecting a defect of a material according to a second aspect of the present invention includes: a step of irradiating X-rays to a material containing fibers as a subject via a plurality of gratings including a first grating to which the X-rays are irradiated and a second grating to which the X-rays that have passed through the first grating are irradiated; a step of detecting an image signal based on the X-rays irradiated to the material; a step of acquiring a dark field image representing an attenuation rate of interference intensity of the X-rays in a case in which the material is present and in a case in which the material is not present based on the detected image signal; and a step of acquiring information on a defect of the material by a control unit based on the acquired dark field image of the material.

In the method of detecting a defect of a material containing fibers according to the second aspect of the present invention, as described above, by acquiring the information on the defect of the material based on the dark field image of the material, in the step of acquiring the information on the defect of the material, it is possible to omit the step of enlarging the image. As a result, it is possible to relatively quickly and easily detect the ratio of the defect (defective state) in the material.

In the method of detecting a defect of a material containing fibers according to the second aspect of the present invention, preferably, the step of acquiring the information on the defect of the material includes a step of acquiring a total value of luminance values of a pixel line composed of a plurality of pixels along a predetermined direction in the acquired dark field image of the material, acquiring data of a change in the total value along a direction orthogonal to the predetermined direction, and acquiring information on a depth in addition to a length of a crack which is the defect of the material based on the acquired data by the control unit. With this configuration, the step of acquiring the information on the defect of the material includes a step of acquiring the information on the depth in addition to the length of the crack based on the total value of luminance values of each pixel line. Therefore, it is possible to easily detect the region (pixel line) where the defect ratio is large (the damage is large) in the dark field image based on the above information.

In the method of detecting a defect of a material containing fibers in the second aspect of the present invention, preferably, the step of acquiring the information of the defect of the material includes a step of acquiring the information on the defect of the material by the control unit based on a synthesized dark field image obtained by synthesizing a plurality of the dark field images acquired by relatively changing an extending direction of each of a grating component of the first grating and a grating component of the second grating in a grating plane with respect to the material. With such a configuration, by acquiring the synthesized dark field image by relatively changing the extending direction of each of the grating component of the first grating and the grating component of the second grating in the grating plane, as compared with the case in which the information on a defect is acquired from only a single dark field image, it becomes possible to acquire information on more defects.

Further, by obtaining the information on the defect based on the synthesized dark field image, as compared with the case in which information on a defect is individually acquired in each of a plurality of dark field images, the time required for the step of acquiring defect information can be shortened.

BRIEF DESCRIPTION OF THE DRAWINGS

FIG. 5 is a dark field image acquired in a state in which each of the grating component of the first grating (phase grating) and the grating component of the second grating (absorption grating) according to the first embodiment extends in the Y-direction.

FIG. 6A is a dark field image acquired in a state in which each of the grating component of the first grating and the grating component of the second grating extends in the X-direction.

FIG. 6B is a synthesized dark field image captured by synthesizing the dark field image of FIG. 5 and the dark field image of FIG. 6A.

DESCRIPTION OF PREFERRED EMBODIMENTS

Hereinafter, embodiments of the present invention will be described with reference to the drawings.

First Embodiment (Configuration of X-Ray Phase Imaging Apparatus)

A configuration of an X-ray phase imaging apparatus 100 according to a first embodiment will be described with reference to FIG. 1 to FIG. 7.

Figure 1:
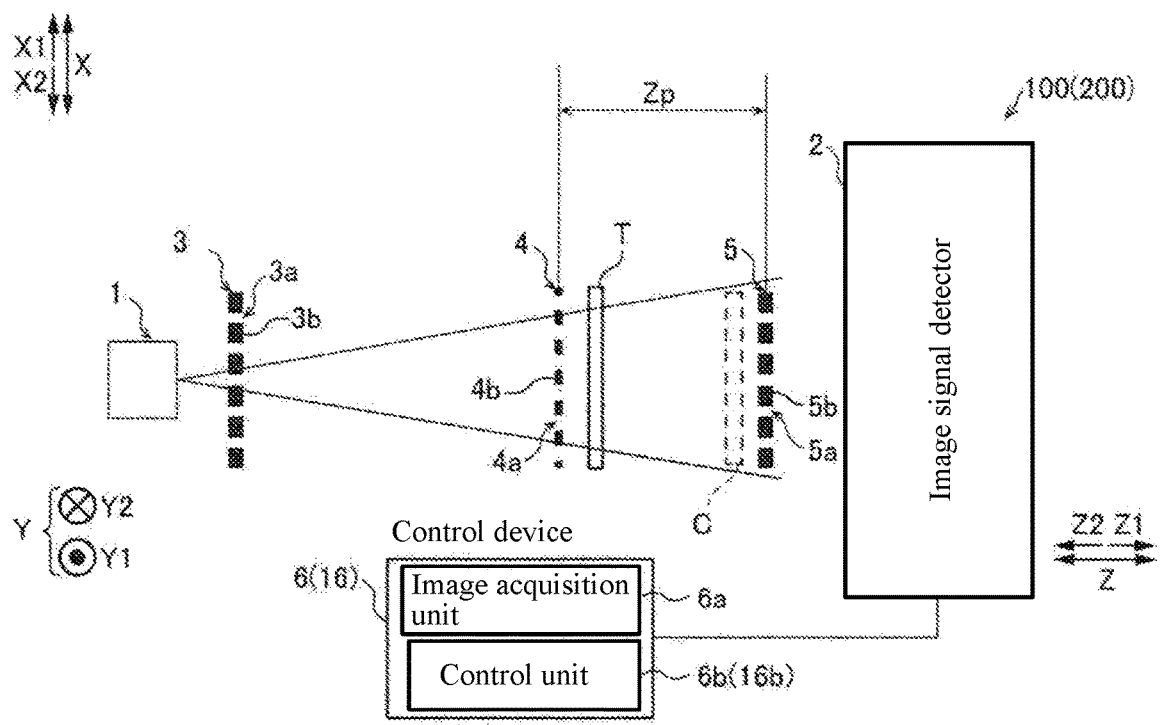
FIG. 1 is a diagram showing an overall structure of an X-ray phase imaging apparatus according to first and second embodiments.

As shown in FIG. 1, the X-ray phase imaging apparatus 100 is an apparatus for imaging an inside of an object by utilizing the phase-contrast of the X-rays that have passed through the object. Further, the X-ray phase imaging apparatus 100 is an apparatus for imaging the inside of the object utilizing a Talbot effect. In this embodiment, a carbon reinforced fiber material T including fibers is inspected as a subject. The carbon reinforced fiber material T contains a resin in addition to carbon fibers (an example of fibers). The carbon reinforced fiber material T may be molded by impregnating carbon fibers with a liquid resin. Note that the method of the forming the carbon reinforced fiber material T is not limited to molding. Note also that while the following description is directed to inspection of the carbon reinforced fiber material T, this is simply one example of the "material" recited in claims—the invention also applies to inspection of other materials and objects.

As shown in FIG. 1, the X-ray phase imaging apparatus 100 is equipped with an X-ray source 1 configured to irradiate X-rays onto the carbon reinforced fiber material T as a subject and an image signal detector 2 configured to detect an image signal based on the X-rays irradiated from the X-ray source 1. The X-ray phase imaging apparatus 100 is also equipped with a plurality of gratings arranged between the X-ray source 1 and the image signal detector 2. Specifically, the plurality of gratings includes a multi-slit 3 for enhancing the coherence of the X-rays irradiated from the X-ray source 1. The plurality of gratings includes a phase grating 4 onto which X-rays from the X-ray source 1 are irradiated and an absorption grating 5 onto which the X-rays that have passed through the phase grating 4 are irradiated. The carbon reinforced fiber material T is placed between the phase grating 4 and the absorption grating 5. Note that the carbon reinforced fiber material T is placed on the Z2-direction side from the center between the phase grating 4 and the absorption grating 5.

Note that in this specification, the direction from the X-ray source 1 toward the multi-slit 3 is defined as a Z1-direction, and the opposite direction thereof is defined as a Z2-direction. Further note that the vertical direction in a plane orthogonal to the Z-direction is defined as an X-direction. In the X-direction, a direction toward the upper side of the paper surface of FIG. 1 is defined as an X1-direction. Further, in the X-direction, a direction toward the lower side of the paper surface of FIG. 1 is defined as an X2-direction. Further, a direction orthogonal to the Z-direction and orthogonal to the X-direction is defined as a Y-direction. In the Y-direction, a direction down into the paper surface of FIG. 1 is defined as a Y2-direction. Also, in the Y-direction, a direction up from the front side of the paper surface of FIG. 1 is defined as a Y1-direction. The phase grating 4 and the absorption grating 5 are an example of the "first grating" and an example of the "second grating" recited in claims, respectively. Further, the multi-slit 3 is an example of the "third grating" recited in claims. Note that FIG. 1 is a diagram schematically illustrated for the purpose of explanation.

Also, the X-ray phase imaging apparatus 100 is provided with a control device 6 configured to receive the detection result of the image signal detector 2. The control device 6 includes an image acquisition unit 6a and a control unit 6b. The control device 6 may comprise a computer and the image acquisition unit 6a and control unit 6b may be modules of the computer, such as software routines configuring the computer. The computer may include, for example, one or more processors configured by software, such as a CPU (Central Processing Unit) GPU, controller, etc. The computer may be a general purpose computer or may be dedicated hardware or firmware (e.g., a digital signal processor (DSP) or a field-programmable gate array (FPGA)). The image acquisition unit 6a and a control unit 6b may comprise a separate computer, or share the hardware of the same computer.

The X-ray source 1 is configured to generate X-rays when a high voltage is applied and irradiate the generated X-rays in the Z1-direction.

The multi-slit 3 includes a plurality of X-ray transmission portions 3a and a plurality of X-ray absorption portions 3b arranged at predetermined periods (pitches) in the X-direction. The X-ray transmission portions 3a may each comprise a slit defined between neighboring ones of the X-ray absorption portions 3b. The X-ray transmission portions 3a and the X-ray absorption portions 3b are each configured to extend in the Y-direction.

The multi-slit 3 is arranged between the X-ray source 1 and the phase grating 4, so that X-rays are irradiated to the multi-slit 3 from the X-ray source 1. The multi-slit 3 is configured to make the X-rays that have passed through each X-ray transmission portion 3a as line light sources so that the X-rays from the X-ray source 1 are converted into a multipoint light source. It is possible to enhance the coherence of the X-rays irradiated from the X-ray source 1 when the pitch and the distance between the gratings of three gratings (the multi-slit 3, the phase grating 4, and the absorption grating 5) satisfy a certain condition. This makes it possible to maintain the interference intensity even if the focal spot size of the tube of the X-ray source 1 is large.

The phase grating 4 is provided with a plurality of slits 4a and a plurality of X-ray phase change portions 4b arranged at predetermined periods (pitches) in the X-direction. The slits 4a and the X-ray phase change portions 4b are each formed so as to have a length that extends in the Y-direction. Note that the X-ray phase change portion 4b is an example of the "grating component of the first grating" recited in claims.

The phase grating 4 is arranged between the multi-slit 3 and the absorption grating 5, and is irradiated with the X-rays that have passed through the multi-slit 3. The phase grating 4 is provided to form a self-image C by a Talbot effect. When X-rays with coherence pass through a grating having slits are formed therein, a grating image (self-image C) is formed at a position away from the grating by a predetermined distance (Talbot distance Zp). This is called a Talbot effect. The self-image C illustrated in FIG. 1 is shown offset from the Talbot distance Zp for purposes of illustration.

The absorption grating 5 has a plurality of X-ray transmission portions 5a and a plurality of X-ray absorption portions 5b arranged at predetermined periods (pitches) in the X-direction. The absorption grating 5 is arranged between the phase grating 4 and the image signal detector 2, and is irradiated with the X-rays that have passed through the phase grating 4. Further, the absorption grating 5 is arranged at a position away from the phase grating 4 by the Talbot distance Zp. The absorption grating 5 interferes with the self-image C of the phase grating 4 to form a moire fringe (not shown) on the detection surface of the image signal detector 2. In the X-ray phase imaging apparatus 100, a method (fringe scanning method) of acquiring a reconstructed image from a plurality of moire fringes (images) acquired by scanning the absorption grating 5 at regular time intervals is used. The detailed explanation of the fringe scanning method will be described later. Note that the X-ray absorption portion 5b is an example of the "grating component of the second grating" recited in claims.

The image signal detector 2 is configured to detect the X-rays, convert the detected X-rays into an electric signal, and read the converted electric signal as an image signal. The image signal detector 2 is, for example, an FPD (Flat Panel Detector). The image signal detector 2 is composed of a plurality of conversion elements (e.g., photodiodes or photoconductors, not shown) and a plurality of pixel electrodes (not shown) arranged on the plurality of conversion elements. The plurality of conversion elements and the plurality of pixel electrodes are arrayed in the X-direction and the Y-direction at predetermined periods. Each pair of a conversion element and a pixel electrode may form pixel of the FPD of a plurality of pixels of the FPD. The FPD may thus comprise a plurality of detection pixels arranged in an array extending in the X and Y directions to provide an image (e.g., a pixelated image in the form of a plurality of pixels corresponding to luminance values provided by the pixels of the FPD). Further, the image signal detector 2 is configured to output the acquired image signal to the control device 6.

The X-ray phase imaging apparatus 100 is equipped with an image acquisition unit 6a configured to acquire a dark field image representing an attenuation rate of X-ray interference intensity in a case in which the carbon reinforced fiber material T exists and in a case in which the carbon reinforced fiber material T is not present based on the image signal detected by the image signal detector 2. Further, the image acquisition unit 6a acquires an absorption image and a phase differential image. The image acquisition unit 6a is provided in the control device 6.

(Fringe Scanning Method)

Here, in this embodiment, the image acquisition unit 6a acquires a dark field image by moving the absorption grating 5 in a direction orthogonal to the direction (Y-direction in FIG. 1) in which each of the X-ray phase change portion 4b of the phase grating 4 and the X-ray absorption portion 5b of the absorption grating 5 extends and a direction (X-direction in FIG. 1) orthogonal to the optical axis direction (Z-direction in FIG. 1) of the X-rays. The description herein refers to moving the absorption grating 5, however, movement of phase grating 4 may also or instead be performed to obtain the relative movement between the absorption grating 5 and the phase grate 4 described herein. A specific method will be described in detail below.

Hereinafter, acquisition of an absorption image, a phase differential image, and a dark field image by a fringe scanning method will be described with reference to FIG. 2 to FIG. 4. The absorption image, the phase differential image, and the dark field image can be obtained by comparing the X-ray image when the subject is not placed (hereinafter referred to as an "X-ray image Ir") with the X-ray image when the subject is placed between the phase grating 4 and the absorption grating 5 (hereinafter referred to as an "X-ray image Is").

Figure 2A:
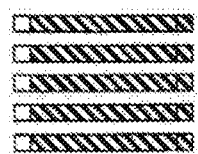
FIG. 2A is a diagram showing a state in which a self-image and a grating component of a second grating (absorption grating) according to the first and second embodiments are arranged in a superimposed manner.
Figure 2B:
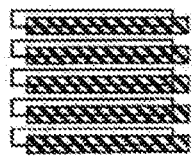
FIG. 2B is a diagram showing a state in which a self-image and a half of a grating component of a second grating (absorption grating) according to the first and second embodiments are arranged in a superimposed manner.
Figure 2C:
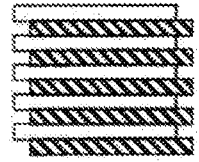
FIG. 2C is a diagram showing a state in which a self-image and a grating component of a second grating (absorption grating) according to the first and second embodiments are arranged in a non-superimposed manner.

The X-ray image Ir and the X-ray image Is are captured multiple times by moving the absorption grating 5 in the X-direction (changing the grating position). For comparison, the X-ray image Ir and the X-ray image Is are captured at the same corresponding grating position. FIG. 2A, FIG. 2B, and FIG. 2C show the positional relationship between the self-image C caused by the phase grating 4 and the absorption grating 5. FIG. 2A to FIG. 2C are views seen from the X-ray imaging direction. In the self-image C, the inside of the rectangle shape shown in white corresponds to the part where X-rays are strengthened by interference, and the other parts correspond to a part where the X-rays are weakened by interference. As shown in FIG. 2A to FIG. 2C, the self-image C (which is a grating image at the Talbot distance Zp (see FIG. 1)) is a stripe of bright and dark X-rays reflecting the shape of the phase grating 4. Further, in the absorption grating 5, the inside of the rectangular shape is represented by hatching and corresponds to the X-ray absorption portion 5b (see FIG. 1).

Here, the absorption grating 5 is configured so as to be substantially or fully overlapped with the self-image C. Therefore, as shown in FIG. 2A, it is possible to block the X-rays of the self-image C by superimposing the self-image C and the X-ray absorption portion 5b (see FIG. 1) of the absorption grating 5. For the sake of clarity, however, the absorption grating 5 is shown in a manner as to be slightly offset from one another in the lateral direction (Y-direction). By moving the absorption grating 5 in the vertical direction (X-direction) at constant intervals, the X-ray image Ir and the X-ray image Is are captured at each grating position. FIG. 2B shows the state in which the absorption grating 5 is shifted downward so as to be overlapped with the self-image C by approximately half. Further, FIG. 2C shows a state in which the absorption grating 5 is shifted further downward so as not to be overlapped with the self-image C.

Figure 2D:
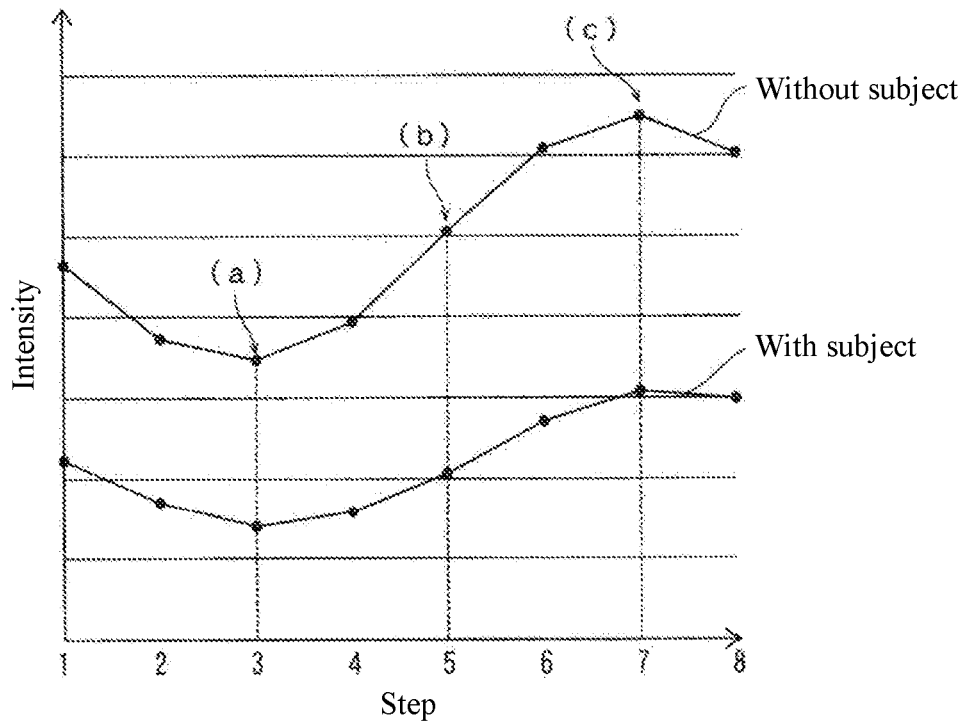
FIG. 2D is a diagram for explaining a step curve of the X-ray phase imaging apparatus according to the first and second embodiments.

FIG. 2D shows a step curve of the pixel value (luminance value representing the magnitude of the X-ray detection amount) of one pixel of an X-ray image Ir and an X-ray image Is corresponding to each grating position (each step) acquired in a state in which the subject exists on the path of the X-rays and in a state in which the subject does not exist on the path of the X-rays. The two step curves of the case in which the subject exists (X-ray image Ir) and the case in which the subject does not exist (X-ray image Is) are compared for each pixel. Based on the comparison, an absorption image, a phase differential image, and a dark field image are obtained. Specifically, an image obtained by imaging the ratio of the average intensity in each image is an absorption image. Further, an image obtained by imaging the magnitude of the phase change of the step curve in each image is a phase differential image. A dark field image is an image obtained by standardizing the attenuation rate of the amplitude of the step curve in each image by the effect of absorption (attenuation rate of the mean value of the step curve).

Here, in the first embodiment, the X-ray phase imaging apparatus 100 (see FIG. 1) is provided with a control unit 6b (see FIG. 1) for obtaining information on the defect of the carbon reinforced fiber material T based on the dark field image of the carbon reinforced fiber material T (see FIG. 1) acquired by the image acquisition unit 6a (see FIG. 1). Specifically, the defect of the carbon reinforced fiber material T is exemplified by a crack of the carbon reinforced fiber material T, impregnation failure of a resin of the carbon reinforced fiber material T, and delamination.

Figure 3:
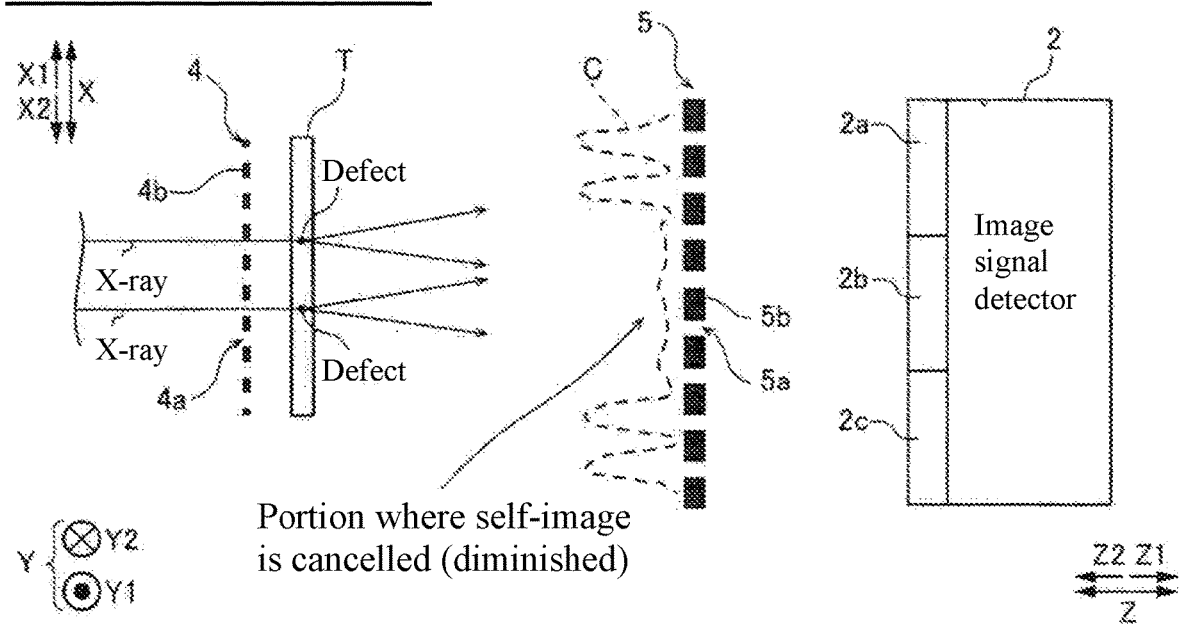
FIG. 3 is a diagram for explaining a state of a self-image in cases where there is a defect in a material according to the first and second embodiments.
Figure 4:
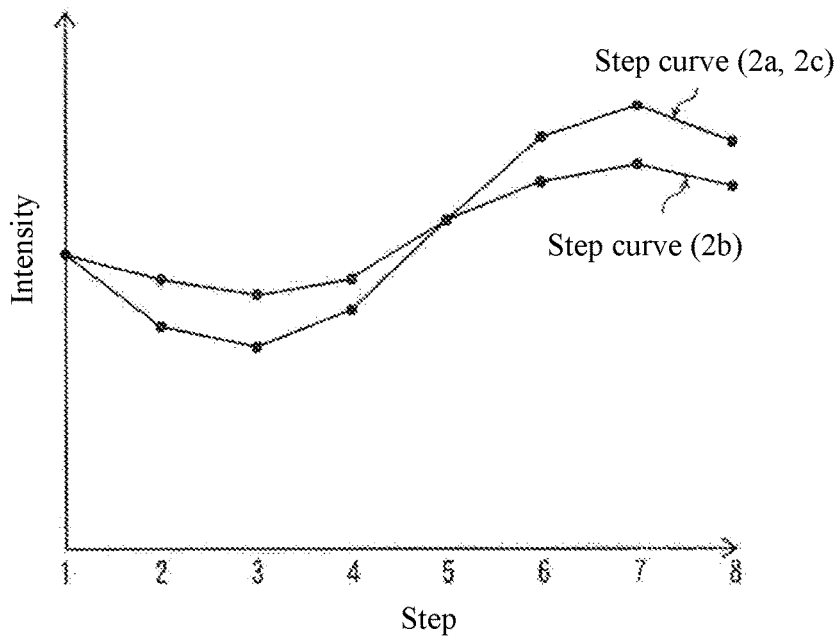
FIG. 4 is a diagram for explaining a step curve in cases where there is a defect in a material according to the first and second embodiments.

Specifically, as shown in FIG. 3, when a defect (crack, resin impregnation failure, or delamination) occurs in the carbon reinforced fiber material T, a layer of air may be formed in the carbon reinforced fiber material T. Further, when X-rays are irradiated onto the carbon reinforced fiber material T containing cracks or resin impregnation failure, X-ray scattering (diffusion) occurs between the layer of the air and the resin or the carbon fibers due to the difference between the refractive index of air and the refractive index of the resin or the carbon fibers. Due to the scattering (diffusion) of X-rays that occurs at this time, the self-image C occurring in the vicinity of the position where absorption grating 5 is arranged is partially canceled (diminished or eliminated) and the intensity (interference intensity) of the self-image C is weakened at the portion where the self-image C (interference fringe) is canceled. As a result, in the self-image C, the difference between the interference intensity of the portion corresponding to the defect and the interference intensity of the other portion becomes relatively large.

As a result, the luminance value of the dark field image in the image (2b) of the image signal detector 2 corresponding to the part (the part corresponding to the defect) where cancellation of the self-image C has occurred becomes lower than the luminance value of the dark field image in the image (2a, 2c) corresponding to the part (the part other than the part corresponding to the defect) where no cancellation of the self-image C has occurred. That is, the amplitude of the step curve (see FIG. 4) in the image (2b) becomes smaller than the amplitude of the step curve (see FIG. 4) in the image (2a, 2c). The period of the absorption grating 5 and the period of the self-image C are designed to be equal to each other and sufficiently smaller than the size (the size in the X-direction and the Y-direction) of the pixel (2a to 2c) of the image signal detector 2. Note that FIG. 3 is a diagram schematically illustrated for the purpose of explanation. Further note that, in FIG. 3, the self-image C is schematically illustrated by a waveform representing the intensity of the self-image C (the portion protruding toward the Z2-direction side is higher in the intensity of the self-image C).

Further, the control unit 6b (see FIG. 1) analyzes the dark field image acquired on the basis of the scattering (diffusion) of the X-rays occurred between the layer of air and the resin or the carbon fibers to thereby obtain the information on cracks, impregnation failure of the resin, and delamination. In FIG. 5, cracks of the carbon reinforced fiber material T, a resin impregnation defective part of the carbon reinforced fiber material T, and delamination portions are shown as black streaks. As shown in FIG. 5, in the dark field image obtained in a state in which each of the X-ray phase change portion 4b (see FIG. 1) and the X-ray absorption portion 5b (see FIG. 1) extends in the Y-direction, a defect extending in the lateral direction (Y-direction) and a defect extending obliquely appear in the dark field image.

Further, in the first embodiment, as shown in FIG. 5, the control unit 6b (see FIG. 1) is configured to acquire the information on the length and the quantity of one or more defects (such as crack(s), resin impregnation defective part(s), and delamination part(s)) of the carbon reinforced fiber material T based on the dark field image of the carbon reinforced fiber material T (see FIG. 1) acquired by the image acquisition unit 6a (see FIG. 1). Specifically, the control unit 6b first extracts pixels whose luminance is equal to or less than a predetermined threshold value in the dark field image. Since a defect appears as a black streak in the dark field image, by extracting pixels with a relatively low luminance value, pixels corresponding to one or more defects exists are extracted. The control unit 6b may identify groups of the extracted pixels define a line of extracted pixels (e.g., a clustering of extracted pixels that are on or within a predetermined threshold distance of a line). Next, for each such group of extracted pixels, the control unit 6b performs a thinning process (a process of thinning the line so as to leave only the portion corresponding to the center of the line) based on the extracted pixels. This thinning process results in a line segment identifying a corresponding defect. Based on the result of this thinning process (a line segment obtained by the thinning process for each defect), the length of each defect and the quantity of the defects are automatically calculated by the control unit 6b. When a plurality of defects is extracted, the length of each defect is calculated. Note that the length of the defect means the size of the defect in the XY-plane. Although this example is described in connection with detecting linear defects (e.g., corresponding to a line segment), defects having other shapes may be detected. It is possible to determine a total path length of each defect in the XY-plane may be obtained. In addition, for each defect, the linear distance from a first end of the defect to a second end of the defect in the XY-plane may be obtained.

Further, in the first embodiment, as shown in FIGS. 6A and 6B, the control unit 6b (see FIG. 1) is configured to perform fringe scanning by relatively changing the extending direction of each of the X-ray phase change portion 4b (see FIG. 1) of the phase grating 4 and the X-ray absorption portion 5b (see FIG. 1) of the absorption grating 5 with respect to the carbon reinforced fiber material T (see FIG. 1) and acquire a plurality of dark field images, each corresponding to different such extending directions relative to the carbon reinforced fiber material T. "Extending direction" as used herein refers to the direction of the length of an element, where the length dimension is greater than first and second width dimensions of the element, where the length dimension, first width dimension and second width dimension are all orthogonal to each other. A synthesized dark field image may be obtained by synthesizing the acquired plurality of dark field images and information of one or more defects of the carbon reinforced fiber material T may be obtained based on the synthesized dark field image. Hereinafter, the details of one example will be described.

First, a first dark field image may be obtained as described with respect to FIG. 5. Then, in a state in which each of the X-ray phase change portion 4b (see FIG. 1) and the X-ray absorption portion 5b (see FIG. 1) extends in the X-direction by rotating the phase grating 4 (see FIG. 1) and absorption grating 5 (see FIG. 1) by 90 degrees, a second dark field image (see FIG. 6A) is acquired by the image acquisition unit 6a (see FIG. 1). In this case, the multi-slit 3 (see FIG. 1) is also rotated by 90 degrees so that the X-ray absorption portion 3b (see FIG. 1) of the multi-slit 3 extends in the X-direction. As shown in FIG. 6A, in the dark field image obtained in a state in which each of the X-ray phase change portion 4b and the X-ray absorption portion 5b extends in the X-direction, mainly, a defect extending in the vertical direction (X-direction) and a defect extending oblique to the X-direction appear in the dark field image.

Then, the image acquisition unit 6a (see FIG. 1) synthesizes the first dark field image (see FIG. 5) (obtained in a state in which each of the X-ray phase change portion 4b (see FIG. 1) and the X-ray absorption portion 5b (see FIG. 1) extends in the Y-direction) and the second dark field image (see FIG. 6A) (obtained in a state in which each of the X-ray phase change portion 4b and the X-ray absorption portion 5b extends in the X-direction. As shown in FIG. 6B, in the synthesized dark field image, each of a defect extending in the vertical direction (X-direction), a defect extending in the lateral direction (Y-direction), and a defect extending in the oblique direction appears. Then, based on the acquired synthesized dark field image (see FIG. 6B), the control unit 6b acquires the information on the one or more defects (the length of each defect and the quantity of the defects) of the carbon reinforced fiber material T (see FIG. 1). Note that the synthesized dark field image can be acquired by calculating the square root value of the sum of squares of the data of each dark field image. For example, each luminance value $i_{(x, y)}$ of each pixel at a location having coordinates (x, y) of the synthesized dark field image may be calculated as the square root of $((i_{(x1, y1)}^2 + i_{(x2, y2)}^2)/2)$ where $i_{(x1, y1)}$ and $i_{(x2, y2)}$ are the respective luminance values of a pixel at the (x, y) coordinate location of the first dark field image and the second dark field image, respectively.

(Acquisition Flow of Defect Information of Carbon Reinforced Fibers)

Figure 7:
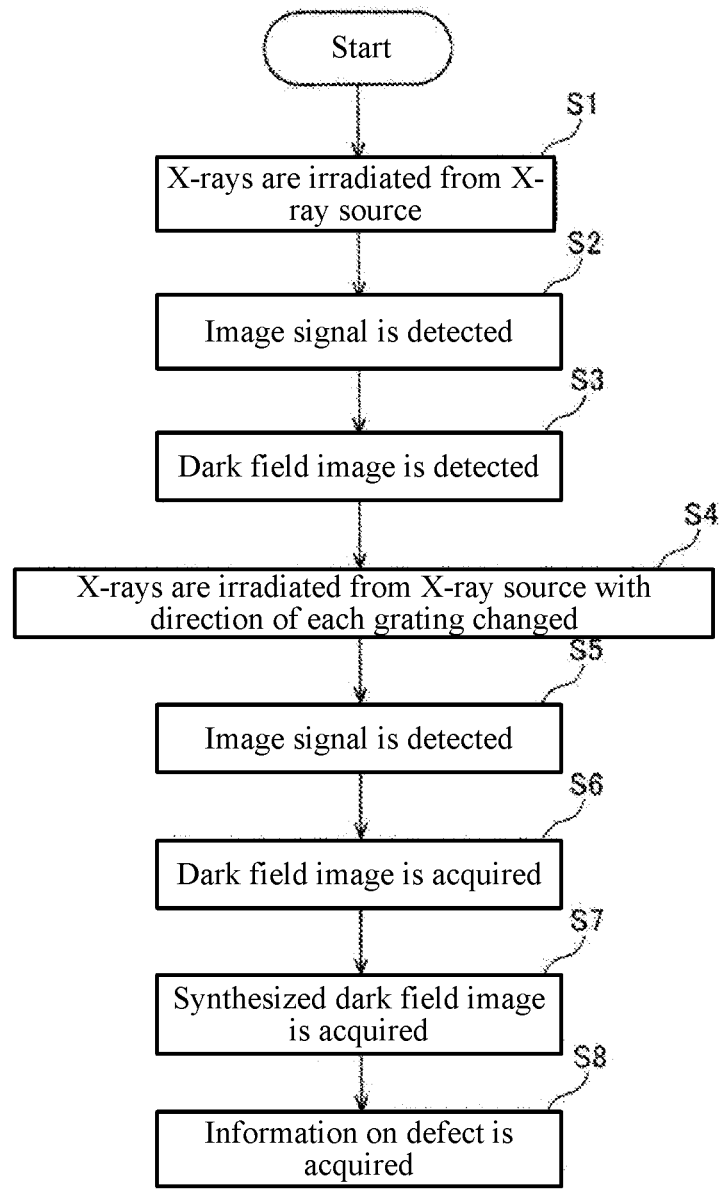
FIG. 7 is a diagram for explaining a flow of acquiring information of a defect of a material of the X-ray phase imaging apparatus according to the first embodiment.

Next, with reference to FIG. 7, an acquisition flow of information on a defect of the carbon reinforced fiber material T by the X-ray phase imaging apparatus 100 (see FIG. 1) according to the first embodiment will be described.

First, in Step S1, X-rays are irradiated from the X-ray source 1 onto the carbon reinforced fiber material T. Specifically, X-rays are irradiated from the X-ray source 1 to the carbon reinforced fiber material T via the multi-slit 3, the phase grating 4, and the absorption grating 5. Note that in Step S1, the step is performed in a state in which the X-ray phase change portion 4b and the X-ray absorption portion 5b extend in the Y-direction.

Next, in Step S2, the image signal detector 2 performs fringe scanning, and in Step S1, it detects an image signal based on the X-rays irradiated to the carbon reinforced fiber material T.

Next, in Step S3, the image acquisition unit 6a acquires the dark field image based on the image signal detected by the image signal detector 2.

Next, in Step S4, X-rays are irradiated from the X-ray source 1 to the carbon reinforced fiber material T in a state in which each of the X-ray phase change portion 4b and the X-ray absorption portion 5b extends in the X-direction.

Next, in Step S5, the image signal detector 2 performs fringe scanning, and in Step S4, it detects an image signal based on the X-rays irradiated onto the carbon reinforced fiber material T.

Next, in Step S6, the image acquisition unit 6a acquires the dark field image based on the image signal detected by the image signal detector 2 in Step S5.

Next, in Step S7, the image acquisition unit 6a synthesizes the dark field image acquired in Step S3 and the dark field image acquired in Step S6 to acquire a synthesized dark field image.

Then, in Step S8, the control unit 6b acquires the information on the defect of the carbon reinforced fiber material T based on the synthesized dark field image acquired in Step S7.

(Effects of First Embodiment)

In the first embodiment, the following effects can be obtained.

In the first embodiment, as described above, the X-ray phase imaging apparatus 100 is equipped with a plurality of gratings arranged between the X-ray source 1 and the image signal detector 2. The plurality of gratings includes the phase grating 4 to which the X-rays from the X-ray source 1 are irradiated and the absorption grating 5 to which the X-rays which have passed through the phase grating 4 are irradiated. The X-ray phase imaging apparatus 100 is configured to include the image acquisition unit 6a for acquiring the dark field image representing the attenuation rate of the X-ray interference intensity in a state in which the carbon reinforced fiber material T is present and in a state in which the carbon reinforced fiber material T is not present based on the image signal detected by the image signal detector 2 and the control unit 6b for acquiring the information on the defect of the carbon reinforced fiber material T based on the dark field image of the carbon reinforced fiber material T acquired by the image acquisition unit 6a.

Here, in an X-ray phase imaging apparatus 100 in which X-rays are irradiated onto the carbon reinforced fiber material T via a plurality of gratings, in cases where X-rays are irradiated onto the carbon reinforced fiber material T in which minute defects are present, X-rays are refracted due to the difference between the refractive index in the defect and the refractive index around the defect. Furthermore, in cases where the boundary between the inside of the defect and the peripheral portion thereof has a complicated shape, X-rays will be multiply refracted to be diffused depending on the shape. In this case, the self-image C (interference fringe formed when X-rays have passed through the phase grating 4) formed in the vicinity of the position where the absorption grating 5 is arranged is partially weakened in the interference intensity by the diffusion of X-rays. As a result, in the self-image C (interference fringe), the difference between the interference intensity of the portion corresponding to the defect and the interference intensity of the other portion becomes relatively large.

Note that the dark field image is obtained from the step curve (the curve representing the change in luminance value when the absorption grating 5 is moved relative to the interference fringe) obtained based on the interference intensity. Therefore, by acquiring information on the defect of the carbon reinforced fiber material T based on the dark field image acquired based on the interference intensity, even if the size of the defect is smaller than the pixel size of the image signal detector 2 and therefore the defect cannot be detected by the absorption image, in the self-image C (interference fringe), the difference between the interference intensity of the portion corresponding to the defect and the interference intensity of the other portion becomes relatively large. Therefore, the defect can be detected by the dark field image. Therefore, the dark field image is particularly useful for detecting a defect of a light element that is less likely to be contrasted in an absorption image.

Further, the pitch of the interference fringe is as small as a few µm, so it is possible to capture micro diffusion of the X-rays due to the defect. Further, the period of the absorption grating 5 is designed to be equal to the pitch of the interference fringe. This makes it possible to capture the diffusion of X-rays based on the change in the step curve by fringe scanning even in the case of a detector having a pixel size much larger than the pitch of the interference fringe and the period of the absorption grating 5. Therefore, by configuring such that the control unit 6b acquires the information on the defect of the carbon reinforced fiber material T based on the dark field image of the carbon reinforced fiber material T acquired by the image acquisition unit 6a, it becomes possible to acquire the information on the defect of the carbon reinforced fiber material T based on the dark field image without enlarging the image. That is, it is possible to acquire the information on the defect of the carbon reinforced fiber material T while suppressing restriction of the observable field of view at one time. As a result, it is possible to easily observe the entire length of a relatively long defect, and it is possible to easily detect the defect ratio (damage degree) in the entire carbon reinforced fiber material T.

Generally, in an X-ray CT apparatus or the like, in the case of observing a light element like a carbon fiber reinforced plastic, in many cases, X-rays of an energy region of soft X-rays are used. In such a case, when a subject is thick, the energy of X-rays that pass through the object becomes high, so that it is difficult to give contrast. On the other hand, in an X-ray phase imaging apparatus in which X-rays are irradiated to a material via a plurality of gratings, in general, X-rays with slightly higher energy than the region of energy of soft X-rays often arrive at the detector. Nevertheless, the refraction and diffusion of X-rays due to the defect in the subject can be captured. Thus, in the X-ray phase imaging apparatus 100, even for a relatively thick material or a material covered with some material, it is possible to easily observe the carbon reinforced fiber material T with X-rays.

Further, in the first embodiment, as described above, the X-ray phase imaging apparatus 100 is configured such that the control unit 6b acquires the information on at least either one of the length and the quantity of one or more cracks which is a defect of the carbon reinforced fiber material T based on the dark field image of the carbon reinforced fiber material T obtained by the image acquisition unit 6a. With this configuration, it is possible to easily detect the ratio of defects (damage state) in the carbon reinforced fiber material T based on at least either one of the length and the quantity of the crack(s).

Further, in the first embodiment, as described above, the X-ray phase imaging apparatus 100 is configured such that the control unit 6b acquires the information on at least either one of the length and the quantity of one or more resin impregnation defective parts which is a defect of the carbon reinforced fiber material T based on the dark field image of the carbon reinforced fiber material T obtained by the image acquisition unit 6a. With this configuration, in addition to the defect of fibers, based on at least either one of the length and the quantity of the impregnation defective part(s) of the resin, it is possible to easily detect the rate of the defect (damage state) in the carbon reinforced fiber material T.

Further, in the first embodiment, as described above, the X-ray phase imaging apparatus 100 is configured such that the control unit 6b acquires the information on the defect of the carbon reinforced fiber material T based on the dark field image acquired by the image acquisition unit 6a by moving the absorption grating 5 in a direction orthogonal to the optical axis direction of the X-rays. Here, in general, in a method (so-called fringe scanning method) of acquiring a dark field image by moving the absorption grating 5 in a direction orthogonal to the optical axis direction of the X-rays, as compared with a method of acquiring a dark field image by rotating the absorption grating 5 in a plane orthogonal to the optical axis direction of the X-rays (so-called moire single imaging method), it is possible to obtain a clear image. That is, the fringe scanning method is particularly effective for detecting minute defects in the carbon reinforced fiber material T.

Further, in the first embodiment, as described above, the X-ray phase imaging apparatus 100 is configured such that the control unit 6b performs fringe scanning by relatively changing the extending direction of each of the X-ray phase change portion 4b of the phase grating 4 and the X-ray absorption portion 5b of the absorption grating 5 with respect to the carbon reinforced fiber material T and acquire the information on the defect of the carbon reinforced fiber material T based on the synthesized dark field image obtained by synthesizing the plurality of dark field images acquired by the image acquisition unit 6a. Here, the defect formed in the direction in which each of the X-ray phase change portion 4b of the phase grating 4 and the X-ray absorption portion 5b of the absorption grating 5 extends is mainly acquired in the dark field image. Therefore, by acquiring a synthesized dark field image by relatively changing the extending direction of each of the X-ray phase change portion 4b of the phase grating 4 and the X-ray absorption portion 5b of the absorption grating 5, as compared with the case in which information on a defect is acquired from only a single dark field image, it is possible to acquire information on more defects.

Further, by acquiring the information on the defect based on the synthesized dark field image, as compared with a case in which the information on the defect is individually acquired plural times in each of a plurality of dark field images, in case of acquiring the information on a defect once in the synthesized dark field image, the required time can be shortened.

Further, in the first embodiment, as described above, the X-ray phase imaging apparatus 100 is configured such that the plurality of gratings is arranged between the X-ray source 1 and the phase grating 4 and includes the multi-slit 3 for enhancing the coherence of the X-rays irradiated from the X-ray source 1. Here, in an X-ray phase imaging apparatus, in some cases, the focal spot size of the X-ray source is reduced in order to enhance the coherence of X-rays. In this case, since the dose from the X-ray source is reduced, the time required for the measurement sometimes becomes longer. Therefore, by providing the multi-slit 3 for enhancing the coherence of the X-rays irradiated from the X-ray source 1, it is possible to enhance the coherence of the X-rays without reducing the focal spot size of the X-ray source 1. With this, as compared with the case of reducing the focal spot size of the X-ray source, it becomes possible to shorten the time required to acquire the information on the defect of the carbon reinforced fiber material T.

Further, in the first embodiment, as described above, a method of detecting a defect of a material including fibers is configured to include: a step of irradiating X-rays to the carbon reinforced fiber material T including fibers as a subject via a plurality of gratings including a phase grating 4 to which the X-rays are irradiated and an absorption grating 5 to which the X-rays that have passed through the phase grating 4 are irradiated; a step of detecting an image signal based on the X-rays irradiated on the carbon reinforced fiber material T; a step of acquiring a dark field image representing an attenuation rate of interference intensity of the X-rays in a case in which the material is present and a case in which the material does not exist based on the detected image signal; and a step of acquiring information on a defect of the material by the control unit 6b based on the acquired dark field image of the carbon reinforced fiber material T. With this, the control unit 6b obtains the information on the defect of the carbon reinforced fiber material T based on the dark field image of the carbon reinforced fiber material T. Therefore, in the step of acquiring the information on the defect of the carbon reinforced fiber material T, the step of enlarging the image can be omitted. As a result, it is possible to relatively quickly and easily detect the ratio of the defect (damage degree) in the carbon reinforced fiber material T.

Further, in the first embodiment, as described above, the method of detecting a defect of a material containing fibers is configured such that the step of acquiring the information on the defect of the carbon reinforced fiber material T includes a step of acquiring the information on the defect of the carbon reinforced fiber material T by the control unit 6b based on the synthesized dark field image obtained by synthesizing a plurality of dark fields acquired by relatively changing the extending direction of each of the X-ray phase change portion 4b of the phase grating 4 and the X-ray absorption portion 5b of the absorption grating 5 in the grating plane for the carbon reinforced fiber material T. Therefore, since the synthesized dark field image is acquired by relatively changing the extending direction of each of the X-ray phase change portion 4b of the phase grating 4 and the X-ray absorption portion 5b of the absorption grating 5 in the grating plane, as compared with the case in which information on a defect is acquired from only a single dark field image, it is possible to acquire information on more defects.

Further, since the information on the defect is obtained based on the synthesized dark field image, as compared with the case in which information on a defect is individually acquired in each of a plurality of dark field images, the time required for the step of acquiring the information on the defect is can be shortened.

Second Embodiment

Next, a configuration of an X-ray phase imaging apparatus 200 according to a second embodiment of the present invention will be described with reference to FIG. 1, FIG. 8, and FIG. 9. In this second embodiment, unlike the first embodiment in which information on defects is acquired based on the luminance values of each of the plurality of dark field images, information on defects is acquired based on the total value of the luminance values of each pixel line of the dark field image. Note that the same reference numerals are allotted to the same configurations as those of the first embodiment in the drawings, and the description thereof will be omitted.

(Configuration of X-Ray Phase Imaging Apparatus)

As shown in FIG. 1, the X-ray phase imaging apparatus 200 is provided with a control device 16 configured to receive the detection result of the image signal detector 2. The control device 16 is provided with an image acquisition unit 6a and a control unit 16b. The control device 16 may comprise a computer and the image acquisition unit 16a and control unit 16b may be modules of the computer, such as software routines configuring the computer, such as described herein with respect to the first embodiment.

Here, in the second embodiment, as described above, the control unit 16b (see FIG. 1) acquires the total value of luminance values of a pixel line consisting of a plurality of pixels along a predetermined direction (X-direction in FIG. 8) in the dark field image of the carbon reinforced fiber material T (see FIG. 1) acquired by the image acquisition unit 6a. Specifically, the control unit 16b acquires the total value of luminance values from the pixel at the end of the dark field image on the X1-direction side to the pixel at end on the X2-direction side. in this case, the dark field image may be subjected to filter processing such as smoothing. Note that in FIG. 8, a dark field image is shown as an example in which the dark field image is obtained in a state in which each of the X-ray phase change portion 4b (see FIG. 1) and the X-ray absorption portion 5b (see FIG. 1) extends in the X-direction.

In detail, the control unit 16b acquires the total value of luminance values of the pixel line in the image (not shown) obtained by inverting (inverting the brightness and the darkness) the acquired dark field image. In the dark field image, the luminance value of the defect (the crack, the resin impregnation defective part, and the delamination part of the resin) of the carbon reinforced fiber material T becomes low (it looks dark). Therefore, in the image in which the dark field image is inverted, the luminance value of the portion where it exists becomes high.

Figure 8:
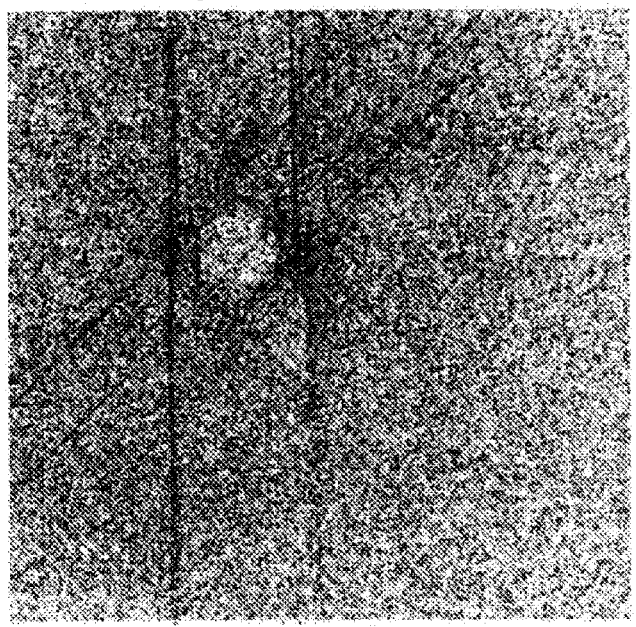
FIG. 8 is a diagram for explaining a method of acquiring data of a total value of luminance values of each pixel line based on the dark field image according to the second embodiment.
Figure 8:
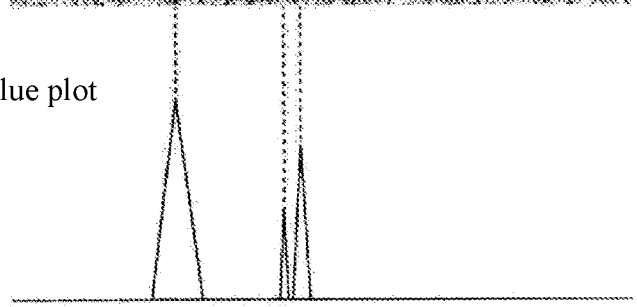
Figure 9:
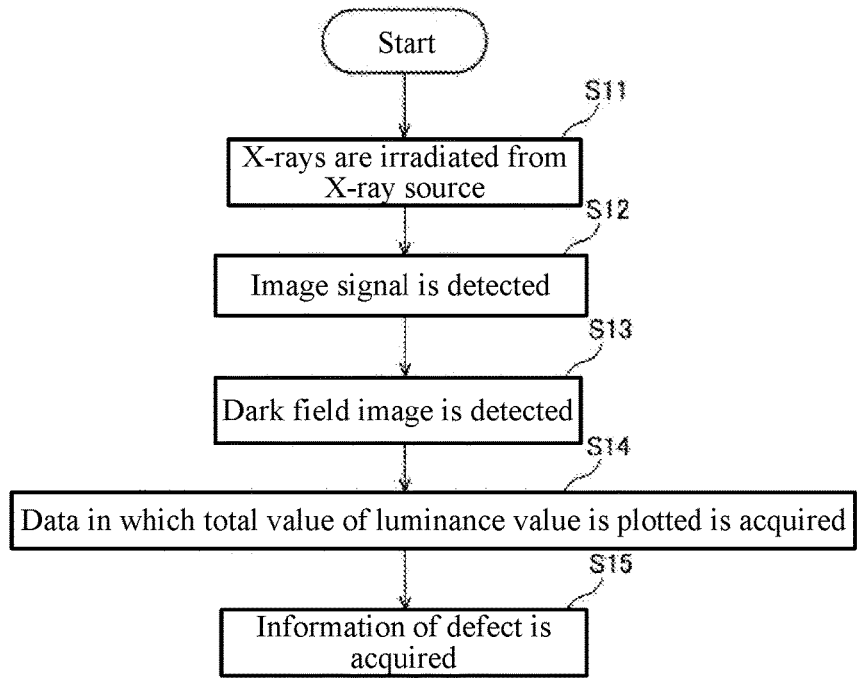
FIG. 9 is a diagram for explaining a flow of acquiring information of a defect of a material of the X-ray phase imaging apparatus according to the second embodiment.
Figure 10A:
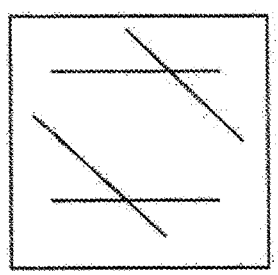
FIG. 10A is a dark field image in the case in which the extending direction of each of the grating component of the first grating and the grating component of the second grating according to a modified example of the first embodiment is the Y-direction.
Figure 10A:
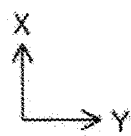
Figure 10B:
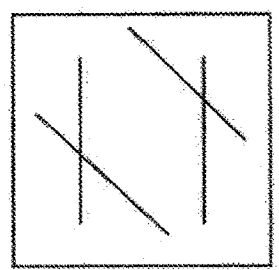
FIG. 10B is a dark field image in the case in which the extending direction of each of the grating component of the first grating and the grating component of the second grating according to a modified example of the first embodiment is the X-direction.
Figure 10B:
Figure 10C:
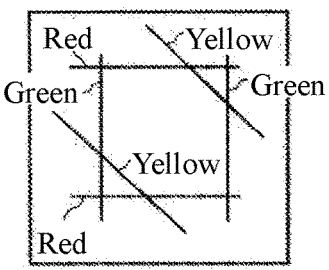
FIG. 10C is a dark field image obtained by synthesizing the dark field image of FIG. 10A and the dark field image of FIG. 10B.
Figure 10C:
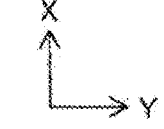

Further, the control unit 16b (see FIG. 1) acquires data of the change of the total value along the direction (Y-direction in FIG. 8) orthogonal to a predetermined direction (for example, the direction in which a defect extends, the X-direction in FIG. 8) (projects the pixel value on the Y-axis). Specifically, the control unit 16b sequentially acquires the total value of luminance values for each of the plurality of pixel lines arranged adjacently along the Y-direction. Then, the control unit 16b acquires the data of the change in the total value of luminance values by plotting the total value of luminance values of each pixel line (with respect to the coordinate in the Y-direction). As a result, in the pixel line where a defect is formed so as to extend in the X-direction exists, since the total value of luminance values becomes relatively large, peaks (three peaks in FIG. 8) appear in the data. In FIG. 8, for the sake of simplicity, it is shown that the total value of luminance values is zero in the pixel lines other than the portion where the peak appears, however, total value of luminance values less than a certain threshold value may indicate absence of a X-direction extending defect at that location.

The control unit 16b (see FIG. 1) is configured to acquire the information on the length, the quantity, and the depth of the defect(s) (a crack(s), a resin impregnation defective part(s), and a delamination part(s)) of the carbon reinforced fiber material T based on the acquired data. That is, the information on the number of defects is acquired based on the number of peaks appearing in the aforementioned data. Also, each of the height of the peak and the area of the peak changes in numerical value corresponding to the length and the depth of the defect. Note that the depth of the defect means the size of the defect in the Z-direction.

Specifically, the deeper the defect, the darker the image (the lower the luminance) in the dark field image. Also, the longer the defect, the larger the number of images where the defect portion exists. That is, the deeper and longer the defect, the larger the total value of the luminance value. Thus, information on the length and the depth of the defect is acquired based on each of the height of the peak and the area of the peak.

(Acquisition Flow of Defect Information of Carbon Reinforced Fibers)

Next, with reference to FIG. 9, an acquisition flow of information on a defect of the carbon reinforced fiber material T (see FIG. 1) by the X-ray phase imaging apparatus 200 (see FIG. 1) according to the second embodiment will be described.

First, in Step S11, X-rays are irradiated from the X-ray source 1 to the carbon reinforced fiber material T.

Next, in Step S12, the image signal detector 2 performs fringe scanning, and in Step S11, it detects an image signal based on the X-rays irradiated to the carbon reinforced fiber material T.

Next, in Step S13, the image acquisition unit 6a acquires the dark field image based on the image signal detected by the image signal detector 2.

Next, in Step S14, the control unit 16b obtains the data obtained by acquiring the total value of luminance values of each pixel line and plotting based on the dark field image acquired in Step S13.

Then, in Step S15, the control unit 16b acquires the information on the defect of the carbon reinforced fiber material T based on the data (data obtained by plotting the total value of luminance values) acquired in Step S14.

(Effects of Second Embodiment)

In the second embodiment, the following effects can be obtained.

In the second embodiment, as described above, the control unit 16b acquires the total value of luminance values of a pixel line consisting of a plurality of pixels along a predetermined direction in the dark field image of the carbon reinforced fiber material T acquired by the image acquisition unit 6a. Further, The X-ray phase imaging apparatus 200 is configured such that the control unit 16b acquires the data of the change of the total value along the direction orthogonal to the predetermined direction and detects the information on the depth of the defect (the crack, the resin impregnation defective part and the part of the delamination) in addition to the depth of the defect. With this, information on the depth of a defect (a crack, a resin impregnation defective part, and a delamination part) is acquired in addition to the length of the defect (the crack, the resin impregnation defective part, and the delamination part) based on the sum of the luminance values of each pixel line. Therefore, the sum of luminance values reflects both the length and the depth of the defect (the crack, the impregnation defective part of resin, and the delamination), so the region (pixel line) where the ratio of the defect is large (damage is large) can be easily detected.

Further, in the second embodiment, as described above, the method of detecting a defect of material containing fibers is configured such that the step of obtaining information on the defect of the carbon reinforced fiber material T includes a step in which the control unit 16b acquires the total value of luminance values of a pixel line consisting of a plurality of images along a predetermined direction in the dark field image of the acquired carbon reinforced fiber material T, acquires the data of the change in the total value along the direction orthogonal to the predetermined direction, and acquires the information on the depth in addition to the length of the defect (a crack, a resin impregnation defective part, and a delamination part) of the carbon reinforced fiber material T based on the acquired data. With this, the step of obtaining the information on the defect of the carbon reinforced fiber material T includes the step of acquiring the information on the depth of the defect (the crack, the resin impregnation defective part, and the delamination part) in addition to the length of the defect (the crack, the impregnation defective part of resin, and the part of delamination) based on the total value of luminance values of each pixel line. Therefore, it is possible to easily detect the region (pixel line) where the defect ratio is large (the damage is large) in the dark field image based on the above information.

Other effects of the second embodiment are the same as those of the first embodiment.

(Modifications)

It should be understood that the embodiments disclosed here are examples in all respects and are not restrictive. The scope of the present invention is shown by the scope of the claims rather than the descriptions of the embodiments described above, and includes all changes (modifications) within the meaning of equivalent and the scope of claims.

For example, in the aforementioned first and second embodiments, an example using a carbon reinforced fiber material T as a material containing fibers is shown, but the present invention is not limited to this. For example, a material containing other fibers (e.g., glass reinforced fibers) may be used.

Further, in the aforementioned first embodiment, an example is shown in which the information on the defect of the material (carbon reinforced fiber material T, e.g.) is acquired based on the synthesized dark field image obtained by synthesizing a plurality of dark field images obtained by relatively changing the extending direction of each of the grating component (X-ray phase change portion 4b) of the first grating (phase grating 4) and the grating component (X-ray absorbing portion 5b) of the second grating (absorption grating 5), but the present invention is not limited thereto. For example, information on the defect of the material (carbon reinforced fiber material T, e.g.) may be obtained based only on a single dark field image.

Further, in the aforementioned first embodiment, an example is shown in which the information on the defect of the material (carbon reinforced fiber material T, e.g.) is acquired based on the synthesized dark field image obtained by synthesizing a dark field image in which the extending direction of each of the grating component (X-ray phase change portion 4b) of the first grating (phase grating 4) and the grating component (X-ray absorption portion 5b) of the second grating (absorption grating 5) is the X-direction and a dark field image in which the extending direction is the Y-direction, but the present invention is not limited thereto. For example, a dark field image in cases where the extending direction of each of the grating component (X-ray phase change portion 4b) of first grating (phase grating 4) and the grating component (X-ray absorbing portion 5b) of the second grating (absorption grating 5) is rotated by a predetermined angle (for example, 45 degrees) from the X-direction (Y-direction) (in the XY-plane) may be further synthesized.

Further, in the first embodiment, an example is shown in which the dark field image in cases where the extending direction of each of the first component (X-ray absorbing portion 4b) of the first grating (phase grating 4) and the grating component (X-ray absorption portion 5b) of the second grating (absorption grating 5) is the X-direction is acquired after acquiring the dark field in cases where extending direction of each of the grating component (X-ray phase change portion 4b) of the first grating (phase grating 4) and the grating component (X-ray absorbing portion 5b) of the first grating (phase grating 4) is the Y-direction, but the present invention is not limited thereto. The order of obtaining the dark field image may be reversed.

Further, in the aforementioned first embodiment, an example is shown in which the synthesized dark field image is obtained by calculating the square root value of sum of squares of the data of the dark field image in which the extending direction of each of the grating component (X-ray phase change portion 4b) of the first grating (phase grating 4) and the grating component (X-ray absorbing portion 5b) of the second grating (absorption grating 5) is the X-direction and a dark field image in which the extending direction is the Y-direction, but the present invention is not limited thereto. For example, as shown in FIG. 10, each dark field image may be simply synthesized without performing an operation based on each dark field image. In this case, the defect appearing in the dark field image (see FIG. 10A) is displayed by the first color (for example, red) in cases where the extending direction of each of the grating component (X-ray phase change portion 4b) of the first grating (phase grating 4) and the grating component (X-ray absorbing portion 5b) of the second grating (absorption grating 5) is the Y-direction and the defect appearing in the dark field image (see FIG. 10B) in the case where the extending direction of the grating component is the X-direction may be displayed in the second color (for example, green). As a result, in the synthesized dark field image (see FIG. 10C) obtained by synthesizing the dark field image of FIG. 10A and the dark field image of FIG. 10B, the obliquely extending defect acquired in both of the dark field images is displayed in the third color (in this case, yellow) which is a mixed color of the first color and the second color.

Further, in the aforementioned first and second embodiments, an example is shown in which the information on the defect of the material (carbon reinforced fiber material T, e.g.) is obtained based on only the dark field image acquired by the image acquisition unit, but the present invention is not limited thereto. For example, the information on the defect of the material (carbon reinforced fiber material T, e.g.) may be acquired based on the image obtained by synthesizing the absorption image and the dark field image acquired by the image acquisition unit. This makes it easy to grasp the whole image of the sample as the subject from the absorption image, so it is possible to more accurately acquire the information (such as the position in the sample) on the defect of the material (carbon reinforced fiber material T, e.g.).

Further, in the aforementioned second embodiment, an example is shown in which the information on the defect of the material (carbon reinforced fiber material T, e.g.) is acquired based on the dark field image in cases where the extending direction of each of the grating component (X-ray phase change portion 4b) of the first grating (phase grating 4) and the grating component (X-ray absorption portion 5b) of the second grating (absorption grating 5) is the X-direction, but the present invention is not limited thereto. For example, the information on the defect of the material (carbon reinforced fiber material T, e.g.) may be acquired based on the dark field image in cases where the extending direction of each of the grating component (X-ray phase change portion 4b) of the first grating (phase grating 4) and the grating component (X-ray absorbing portion 5b) of the second grating (absorption grating 5) is the Y-direction. In this case, the total value of luminance values is sequentially acquired for each of a plurality of pixel lines arranged in the X-direction.

Further, in the second embodiment, an example of acquiring the total value of luminance values of the pixel line extending in the X-direction is shown, but the present invention is not limited to this. For example, the obtained dark field image may be rotated by a predetermined angle, and the total value of luminance values of the pixel line along a predetermined direction of the dark field image after rotation may be acquired. Also, instead of the total value of luminance values of the pixel line extending in a predetermined direction, a total value of luminance values of a linearly interpolated pixel lines may be acquired.

Further, in the aforementioned second embodiment, an example is shown in which the information on the defect of the material (carbon reinforced fiber material T, e.g.) is acquired based only on the dark field image in cases where the extending direction of each of the grating component (X-ray phase change portion 4b) of the first grating (phase grating 4) and the grating component (X-ray absorption portion 5b) of the second grating (absorption grating 5) is the X-direction, but the present invention is not limited thereto. For example, also in the second embodiment, in the same manner as in the first embodiment, the information on the defect of the material (carbon reinforced fiber material T, e.g.) may be acquired based on the synthesized dark field image obtained by synthesizing a plurality of dark field images.

Further, in the second embodiment, an example is shown in which the information on the length and the depth of the defect of the material (carbon reinforced fiber material T, e.g.) is acquired based on only the peak appearing in the data acquired by plotting the total value of luminance values of each pixel line in the dark field image, the present invention is not limited to this example. For example, the information on the depth of the defect may be acquired by dividing the peak height (peak area) calculated by the method described in the second embodiment by the length of the defect obtained in the first embodiment.

Further, in the aforementioned second embodiment, the control unit acquires the total value of luminance values from the pixel at the end of the dark field image on the X1-direction side to the pixel at end on the X2-direction side. For example, the control unit may acquire the total value of the pixel line by limiting to a predetermined region (for example, either one of regions in the case where the dark field image is divided into two in the X-direction) in the dark field image.

Further, in the aforementioned first and second embodiments, an example is shown in which the material (carbon reinforced fiber material T, e.g.) is arranged between the first grating (phase grating 4) and the second grating (absorption grating 5), but the present invention is not limited to this example. For example, the material (carbon reinforced fiber material T, e.g.) may be arranged between the third grating (multi-slit 3) and the first grating (phase grating 4).

In the first and second embodiments, an example is shown in which the third grating (multi-slit 3) is provided, but the present invention is not limited thereto. For example, it may be configured such that the third grating (multi-slit 3) may not be provided.

Further, in the aforementioned first and second embodiments, an example is shown in which the dark field image is acquired by moving the second grating (absorption grating 5) in the direction orthogonal to the direction in which each of the grating component (X-ray phase change portion 4b) of the first grating (phase grating 4) and the grating component (X-ray absorption portion 5b) of the second grating (absorption grating 5) extends and the direction orthogonal to the optical axis direction of the X-rays, but the present invention is not limited thereto. For example, the dark field image may be obtained by moving either one of the first grating (phase grating 4) and the third grating (multi-slit 3).

In the first and second embodiments, an example of acquiring the dark field image by a fringe scanning method is shown, but the present invention is not limited thereto. For example, the dark field image may be acquired by a method (moire one imaging method) in which one of the first grating (phase grating 4), the second grating (absorption grating 5), and the third grating (multi-slit 3) is rotated on a plane orthogonal to the optical axis direction.

For example, in the first and second embodiments, an example is shown in which the first grating is the phase grating but the present invention is not limited to this. For example, the first grating may be an absorption grating.

In the first and second embodiments, an example is shown in which the second grating (absorption grating 5) is moved (stepped) in the direction orthogonal to the extending direction of the grating component of each grating, but the present invention is limited to this. For example, one of gratings may be moved in a direction obliquely crossing the extending direction of the grating component of each grating. In this case, in the direction orthogonal to the extending direction of the grating component of each grating, the amount of movement of the moving grating need only be one period of the moving grating.

Figure 11:
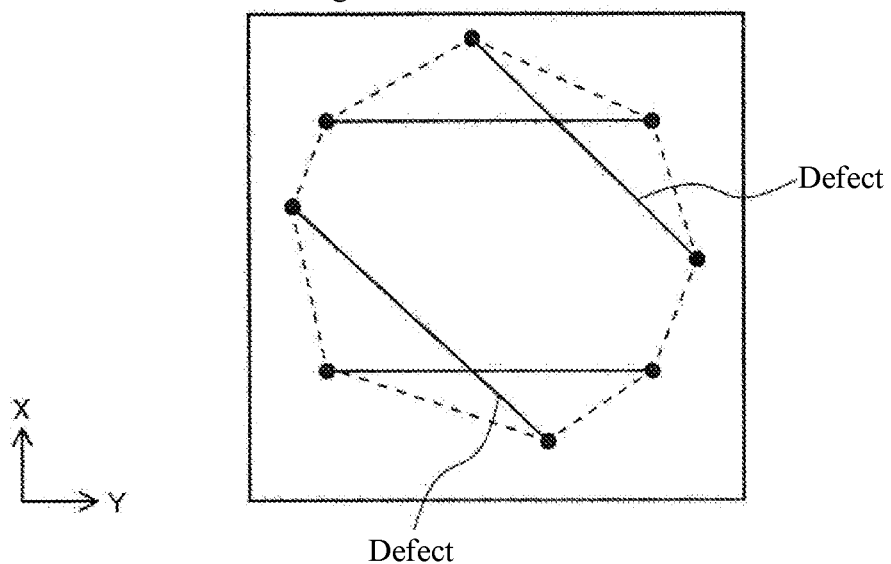
FIG. 11 is a diagram for explaining a method of displaying a region surrounded by defects appearing in a dark field image according to a modification of the first embodiment.

Further, in the first embodiment, an example is shown in which the length and the quantity of the defect(s) are calculated by a thinning process, but the present invention is not limited to this example. For example, as shown in FIG. 11, the control unit 6b (see FIG. 1) may be configured to display the region surrounded by defects of the carbon reinforced fiber material T (the crack, the resin impregnation failure, the delamination, etc.) and acquire the area of the region in the dark field image of the carbon reinforced fiber material T (see FIG. 1) acquired by the image acquisition unit 6a (see FIG. 1). Specifically, the control unit 6b acquires the end portion of the defect in the dark field image (indicated by the black circle in FIG. 11) and connects the ends by line segments (indicated by a broken line in FIG. 11). Then, the control unit 6b displays the region surrounded by the line segment and acquires the area of the region. Thus, by displaying the region and acquiring the area of the region, the damage degree of the carbon reinforced fiber material T can be more clearly grasped.

Further, in the first embodiment, the length and the quantity of the defect(s) are calculated by a thinning process, but the present invention is not limited to this example. For example, the tip of the defect may be detected and the coordinates of the detected tip end may be calculated. In this case, the control unit may be configured to calculate the length and the number of defects based on the calculated defect coordinates.

In the first and second embodiments, an example of acquiring the information of the defect based on the dark field image is shown, but the present invention is not limited thereto. Specifically, in addition to defect information, the control unit may acquire the information on a region whose luminance value of image is equal to or less than a predetermined threshold in the dark field image. For example, in addition to the information on a defect, the control unit may also acquire the information on a region having a luminance value higher by a predetermined amount than the luminance value corresponding to the defect portion. In this case, the control unit may depict a region in the dark field image where the luminance value of the image is equal to or less than a predetermined threshold in the dark field image, or obtain the area of the region.

Further, in the aforementioned first and second embodiments, for the sake of convenience of explanation, the description has been made using the flow driven type flow chart in which the processing of the control according to the present invention is sequentially performed along the processing flow, but the present invention is not limited thereto. In the present invention, the processing operation of the control may be performed by an event driven type (event driven type) processing that executes processing in units of events. In the present invention, the processing operation of the control may be performed by an event driven type (event driven type) processing that executes processing in units of events. In this case, it may be performed in a completely event driven manner or in such a manner as to combine event driving and flow driving.

The invention claimed is:

1. An X-ray phase imaging apparatus comprising:
  an X-ray source configured to irradiate X-rays onto fiber-reinforced plastic as a subject;
  an image signal detector configured to provide an image signal based on the X-rays irradiated from the X-ray source;
  a plurality of gratings arranged between the X-ray source and the image signal detector, the plurality of gratings including a first grating onto which the X-rays from the X-ray source are irradiated and a second grating onto which the X-rays that have passed through the first grating are irradiated;
  an image acquisition unit configured to acquire a dark field image representing an attenuation rate of interference intensity of the X-rays in a case in which the fiber-reinforced plastic is present and in a case in which the fiber-reinforced plastic is not present based on the image signal detected by the image signal detector; and
  a control unit configured to acquire information of a defect of the fiber-reinforced plastic based on the dark field image of the fiber-reinforced plastic acquired by the image acquisition unit,
  wherein the control unit is configured to:
    extract a pixel in which the defect exists based on a predetermined threshold value in the dark field image, and
    calculate at least one of a length and a quantity of the defect by performing a thinning process based on the extracted pixel, or
  wherein the control unit is configured to:
    acquire a total value of luminance values of a pixel line consisting of a plurality of pixels along a predetermined direction in the dark field image, and
    acquire data of a change of the total value along the direction orthogonal to the predetermined direction, and
    acquire information on the number of the defect based on a number of peaks in the acquired data, or
    acquire information on the length and a depth of the defect based on a height of the peaks and an area of the peaks in the acquired data.

2. The X-ray phase imaging apparatus as recited in claim 1, wherein
  the control unit is configured to acquire information on at least one of a length and a quantity of one or more cracks, the one or more cracks comprising the defect of the fiber-reinforced plastic based on the dark field image of the fiber-reinforced plastic acquired by the image acquisition unit.

3. The X-ray phase imaging apparatus as recited in claim 2, wherein
  the control unit is configured to acquire a total value of luminance values of a pixel line comprised of a plurality of pixels along a predetermined direction in the dark field image of the fiber-reinforced plastic acquired by the image acquisition unit, acquire data of a change in the total value along a direction orthogonal to the predetermined direction, and acquire information on a depth in addition to the length of the one or more cracks, which is the defect of the fiber-reinforced plastic, based on the acquired data.

4. The X-ray phase imaging apparatus as recited in claim 1, wherein
  the control unit is configured to display a region containing one or more cracks, the one or more cracks comprising the defect of the fiber-reinforced plastic, and acquire an area of the region in the dark field image of the fiber-reinforced plastic acquired by the image acquisition unit.

5. The X-ray phase imaging apparatus as recited in claim 1, wherein
  the fiber-reinforced plastic includes a resin in addition to the fibers, and
  the control unit is configured to acquire information on at least one of a length and a quantity of one or more impregnation defective parts of the resin, the one or more impregnation defective parts comprising the defect of the fiber-reinforced plastic based on the dark field image of the fiber-reinforced plastic acquired by the image acquisition unit.

6. The X-ray phase imaging apparatus as recited in claim 1, wherein
  the control unit is configured to acquire information on the defect of the fiber-reinforced plastic based on the dark field image acquired by the image acquisition unit by moving either one of the first grating and the second grating in a direction orthogonal to an optical axis direction of the X-rays.

7. The X-ray phase imaging apparatus as recited in claim 1,
wherein the control unit is configured to perform fringe scanning by relatively changing an extending direction of each of a grating component of the first grating and a grating component of the second grating in a grating plane with respect to the fiber-reinforced plastic and acquire information on the defect of the fiber-reinforced plastic based on a dark field image obtained by synthesizing a plurality of the dark field images acquired by the image acquisition unit, and
wherein each of a plurality of dark field images is acquired by the image acquisition unit with a different corresponding extending direction.

8. The X-ray phase imaging apparatus as recited in claim 1, wherein
the plurality of gratings include a third grating disposed between the X-ray source and the first grating to enhance coherence of the X-rays irradiated from the X-ray source.

9. A method of detecting a defect of a fiber-reinforced plastic, comprising:
a step of irradiating X-rays to the fiber-reinforced plastic as a subject via a plurality of gratings including a first grating to which the X-rays are irradiated and a second grating to which the X-rays that have passed through the first grating are irradiated;
a step of detecting an image signal based on the X-rays irradiated to the fiber-reinforced plastic;
a step of acquiring a dark field image of the fiber-reinforced plastic, the dark field image representing an attenuation rate of interference intensity of the X-rays in a case in which the fiber-reinforced plastic is present and in a case in which the fiber-reinforced plastic is not present based on the detected image signal; and
a step of acquiring information on a defect of the fiber-reinforced plastic by a control unit based on a magnitude of a luminance value of the acquired dark field image of the fiber-reinforced plastic.

10. The method of detecting a defect of the fiber-reinforced plastic as recited in claim 9, wherein
the step of acquiring information on the defect of the fiber-reinforced plastic includes a step of acquiring information on at least one of a length and a quantity of one or more cracks, the one or more cracks comprising the defect of the fiber-reinforced plastic, based on the magnitude of a luminance value in the dark field image of the fiber-reinforced plastic.

11. The method of detecting a defect of the fiber-reinforced plastic as recited in claim 9, wherein
the step of acquiring the information on the defect of the fiber-reinforced plastic includes a step of acquiring a total value of luminance values of a pixel line comprised of a plurality of pixels along a predetermined direction in the acquired dark field image of the fiber-reinforced plastic, acquiring data of a change in the total value along a direction orthogonal to the predetermined direction, and acquiring information on a depth in addition to a length of one or more cracks, which is the defect of the fiber-reinforced plastic, based on the acquired data.

12. The method of detecting a defect of the fiber-reinforced plastic as recited in claim 9, wherein
the step of acquiring information on the defect of the fiber-reinforced plastic includes a step of displaying a region containing one or more cracks, the one or more cracks comprising the defect of the fiber-reinforced plastic, and acquiring an area of the region in the dark field image of the fiber-reinforced plastic.

13. The method of detecting a defect of the fiber-reinforced plastic as recited in claim 9, wherein
the fiber-reinforced plastic includes a resin in addition to the fibers, and
the step of acquiring information on the defect of the fiber-reinforced plastic includes a step of acquiring information on at least one of a length and a quantity of one or more impregnation defective parts of the resin, the one or more impregnation defective parts comprising the defect of the fiber-reinforced plastic based on the magnitude of a luminance value in the dark field image of the fiber-reinforced plastic.

14. The method of detecting a defect of the fiber-reinforced plastic as recited in claim 9, wherein
the step of acquiring information on the defect of the fiber-reinforced plastic includes a step of acquiring information on the defect of the fiber-reinforced plastic based on the magnitude of a luminance value in the dark field image by moving at least one of the first grating and the second grating in a direction orthogonal to an optical axis direction of the X-rays.

15. The method of detecting a defect of the fiber-reinforced plastic as recited in claim 9, wherein
the step of acquiring the information of the defect of the fiber-reinforced plastic includes a step of acquiring the information on the defect of the fiber-reinforced plastic by the control unit based on a synthesized dark field image obtained by synthesizing a plurality of dark field images acquired by relatively changing an extending direction of each of a grating component of the first grating and a grating component of the second grating in a grating plane with respect to the fiber-reinforced plastic.

16. An X-ray phase imaging apparatus comprising:
an X-ray source configured to irradiate X-rays onto fiber-reinforced plastic as a subject;
an image signal detector configured to provide an image signal based on the X-rays irradiated from the X-ray source;
a plurality of gratings arranged between the X-ray source and the image signal detector, the plurality of gratings including a first grating onto which the X-rays from the X-ray source are irradiated and a second grating onto which the X-rays that have passed through the first grating are irradiated;
an image acquisition unit configured to acquire a dark field image representing an attenuation rate of interference intensity of the X-rays in a case in which the fiber-reinforced plastic is present and in a case in which the fiber-reinforced plastic is not present based on the image signal detected by the image signal detector; and
a control unit configured to acquire information of a defect of the fiber-reinforced plastic based on the dark field image of the fiber-reinforced plastic acquired by the image acquisition unit,
wherein the image acquisition unit is configured to acquire a plurality of the dark field images while relatively rotating the first grating and the second grating in a grating plane with respect to the fiber-reinforced plastic and acquire a synthesized dark field image by synthesizing the plurality of the dark field images, and wherein the control unit is configured to acquire information of the defect of the fiber-reinforced plastic based on a synthesized dark field image acquired by the image acquisition unit.

* * * * *